US006936009B2

(12) United States Patent
Venkataramani et al.

(10) Patent No.: US 6,936,009 B2
(45) Date of Patent: Aug. 30, 2005

(54) MATCHING LAYER HAVING GRADIENT IN IMPEDANCE FOR ULTRASOUND TRANSDUCERS

(75) Inventors: Venkat Subramaniam Venkataramani, Clifton Park, NY (US); Lionel Monty Levinson, Niskayuna, NY (US); Lowell Scott Smith, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/681,220

(22) Filed: Feb. 27, 2001

(65) Prior Publication Data

US 2002/0161301 A1 Oct. 31, 2002

(51) Int. Cl.[7] .......... A61B 8/0029
(52) U.S. Cl. .......... 600/459; 29/25.35
(58) Field of Search .......... 600/437–472; 29/25.35, 25.42; 310/328, 336

(56) References Cited

U.S. PATENT DOCUMENTS 4,016,530 A * 4/1977 Goll .......... 367/191
4,101,795 A 7/1978 Fukumoto et al.
4,297,607 A 10/1981 Lynnworth et al.
4,635,484 A 1/1987 Lerch
4,771,205 A 9/1988 Mequio
4,881,212 A * 11/1989 Takeuchi .......... 367/152
5,553,035 A * 9/1996 Seyed-Bolorforosh et al. .. 367/140
5,651,365 A * 7/1997 Hanafy et al. .......... 600/457
5,744,898 A * 4/1998 Smith et al. .......... 310/334
5,779,644 A * 7/1998 Eberle et al. .......... 600/463
5,792,058 A * 8/1998 Lee et al. .......... 600/459
5,938,612 A * 8/1999 Kline-Schoder et al. .... 600/459
5,974,884 A * 11/1999 Sano et al. .......... 73/589

OTHER PUBLICATIONS

G. Kossoff, "The Effects of Backing and Matching on the Performance of Piezoelectric Ceramic Transducers," IEEE Trans. on Sonics and Ultrasonics, vol. SU1–13, No. 1, 20 (1966).

* cited by examiner

*Primary Examiner*—Francis J. Jaworski
(74) *Attorney, Agent, or Firm*—Jean K. Testa; Christian G. Cabou

(57) ABSTRACT

A matching layer for ultrasound transducers has a gradient in impedance value from one surface to the other surface of the matching layer. The matching layer is composed of a plurality of sublayers made of composite materials and securely attached together and is disposed on the surface of the transducer element. The first sublayer adjacent to the transducer element has an impedance value less than or equal to that of the transducer element. The last sublayer adjacent to the target has an impedance value greater than or equal to that of the target. The impedance values of the sublayers decrease monotonically from the first to the last sublayer.

29 Claims, 3 Drawing Sheets

MATCHING LAYER HAVING GRADIENT IN IMPEDANCE FOR ULTRASOUND TRANSDUCERS

BACKGROUND OF INVENTION

This invention relates to materials for and methods of producing matching layers for ultrasound transducers. In particular, this invention relates to matching layers for ultrasound transducers that have a gradient in impedance value between the impedance of the transducer material and that of the target.

Ultrasound prober typically are made up of the transducer piezoelectric ceramic elements sandwiched between the backing or damping layer and a set of matching layers. The backing layers prevents the backward emitted sound waves to echo and ring back into the transducer for detection. The matching layer or layers provide the required acoustic impedance gradient for the acoustic energy from the transducer to smoothly penetrate the body tissue and for the reflected acoustic waves (the returning echo) to smoothly return to the transducer for detection. Without the matching layers, the large impedance difference between the acoustic source (about 33 Mrayls) and the target (about 1.5 Mrayls) would result in loss of transmission and receipt of acoustic energy of up to 90 percent at the interface between the source and the target. Typically, the matching layers are designed to have specific impedance values (e.g., about 15 and 3 Mrayls) and are attached to the transducer. The stepwise reduction of the impedance at the interfaces minimizes the loss in the transmission and receipt of the returning acoustic signals. A matching layer structure with a gradient of impedance across its thickness from hat of the transducer elements (about 33 Mrayls) to that of the body tissue (about 1.5 Mrayls) is the ideal structure for zero loss of signal in the absence of any attenuation of the signal by the matching layer itself. Such a layer would also enhance the fractional bandwidth from a typical 70 percent to 90 percent or more. Such a wider bandwidth allows the transducer to be used selectively in the burst excitation mode at more than one frequency with the accompanying freedom to choose higher resolution of the image details or longer penetration of the beam energy. The optimal thickness for each of the matching layers is one-fourth of the wavelength of the central operating frequency of the transducer elements. Thus, the manufacture of the matching layers can be a challenge because of such a small desired thickness. Matching layers thicker than one-quarter wavelength may be used, but they increase the attenuation of the ultrasound intensity with the attendant reduced performance.

A matching layer having an impedance gradient has been proposed in U.S. Pat. No. 5,974,884. A first material having first impedance equal to or lower than the impedance of the transducer material is formed in a matrix of tapered cone-shaped elements. A second material having second impedance equal to or greater than the impedance of the target living tissue is used to fill the interstices of the matrix and form the finished matching layer. Due to the cone shaped of the first material, the impedance of the matching layer decreases continuously from the surface where the bases of the cones reside to the opposite surface where the cone vertices reside. However, the manufacture of such a matching layer having a thickness on the order of one-quarter wavelength using this method is tedious and could be costly.

Therefore, it is desirable to provide ultrasound probe matching layers that are simple to manufacture and that still have a gradient in impedance or an impedance value varying from one surface of the matching layer to the other surface.

SUMMARY OF INVENTION

A matching layer for ultrasound probes comprises a plurality of sublayers attached together. Each of the sublayers has a different impedance value, such that the first sublayer immediately next to the transducer material has an impedance equal to or less than that of the transducer material and the last sublayer immediately next to the target has an impedance value equal to or greater than that of the target. The target is the object of the examination by the ultrasound device. The target may be a living tissue of a patient. Furthermore, the impedance values of the sublayers decrease from the first to the last sublayers. The thickness of the matching layer is designed to be one-quarter wavelength or an odd multiple of one-quarter wavelength of the central frequency of the transducer when it is energized. The thickness of the matching layer may be designed to be within 20 percent of one-quarter wavelength or an odd multiple of one-quarter wavelength of the central frequency of the transducer.

Other features and advantages of the present invention will be apparent from the following detailed description of the preferred embodiments and the accompanying drawings where like numerals refer to like elements.

DETAILED DESCRIPTION

Ultrasound transducer elements are made of piezoelectric materials. One commonly used material for modern ultrasound transducers is lead zirconate titanate (PZT) which has an impedance of about 33 Mrayls. In a medical use of ultrasound equipment, this impedance is about 20 times that of the target body tissue. The present invention provides a matching layer to bridge this large difference in impedance values to improve the sound transmission across the target surface. The matching layer of the present invention comprises a plurality of sublayers securely and intimately attached together. The sublayers are made of different materials or compositions, each having a different impedance value, such that the first sublayer immediately next to the transducer material has an impedance value equal to or less than that of the transducer material and the last sublayer immediately next to the target has an impedance value equal to or greater than that of the target. When the sublayer is made of a composite material, its impedance is a function of the impedance of the components of the composite material. The impedance value of the first sublayer is preferably within about 20 percent of, more preferably within 10 percent of, and most preferably equal to the values of the transducer element material. The impedance value of the last sublayer is preferably within 20 percent of, more preferably within 10 percent of, and most preferably equal to the impedance value of the target.

Figure 1:
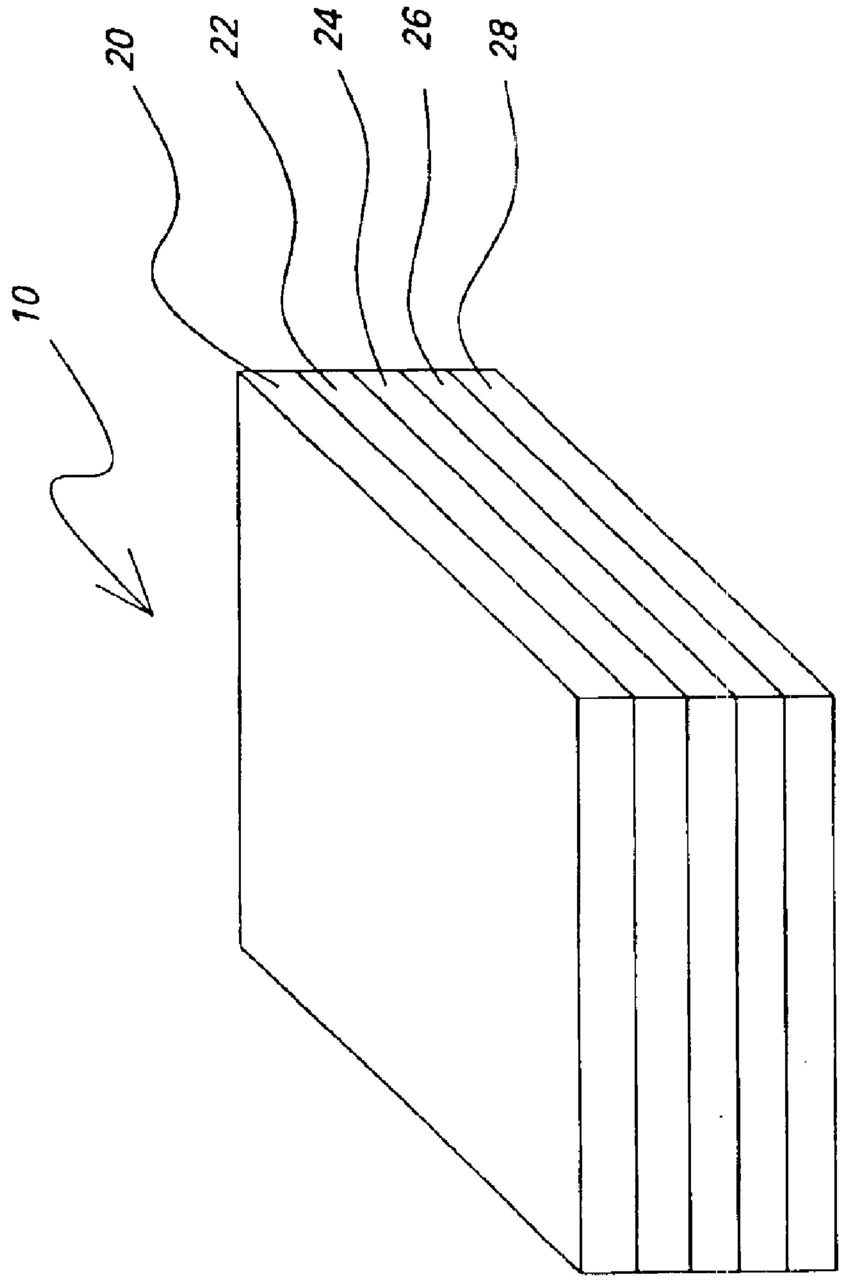
FIG. 1 is a perspective of the first embodiments of the matching layers of the present invention comprising multiple sublayers of different materials.

FIG. 1 shows the first embodiment of the matching layer of the present invention. Matching layer 10 comprises a plurality of sublayers, such as shown by numerals 20–28. For example, matching layer 10 is shown to consists of five sublayers, but any number of sublayers may be used. The number of sublayers will be determined for the desired application so to balance between the increase in transmission at the target surface and the attenuation of the sound within the matching layer. Typically, this number is about 21 or fewer. The sublayers may have the same thickness or different thicknesses. The matching layer preferably has a thickness of one-quarter wavelength or an odd multiple of one-quarter wavelength of the operating frequency of the piezoelectric element when it is energized. The sublayers may be made of materials having decreasing impedance values from that of the piezoelectric element to that of the body tissue. In one embodiment of the present invention, a film of metal serving as the first sublayers, such as Ni, having a thickness of less than about 100 $\mu$m, preferably less than about 75 $\mu$m, more preferably less than about 50 $\mu$m, most preferably less than about 10 $\mu$m, is coated with a thin layer of polymeric material, such as polystyrene, serving as the second sublayer. The polymer sublayer has a thickness of less than about 100 $\mu$m, preferably less than about 75 $\mu$m, more preferably less than about 50 $\mu$m, most preferably less than about 10 $\mu$m. The polymeric material may be deposited on the metal sublayer by electrophoretic deposition. A third sublayer of the same or different metal is deposited on the second sublayer by, for example, electroplating. A fourth sublayer of the same or different polymeric material is deposited on the third sublayer. In this manner, a matching layer is formed having a desired number of sublayers. In one preferred embodiment, the thicknesses of the metal sublayers decrease from the first sublayer, which will be disposed immediately next to the transducer element, to the last sublayer. On the other hand, the thicknesses of the sublayers of the polymeric material or materials increase in the direction from the first to the last sublayer. Other examples of the metals that may be used in the manufacture of the matching layer of the present invention are aluminum, tin, lead, zinc, titanium, iron, cobalt, copper, manganese, chromium, tungsten, gold, silver, magnesium, mixtures thereof, and alloys thereof. Other substances, such as silicon, ceramics, metal compounds, or glass, also may be used in a mixture or alloy with one or more of the metals mentioned above. Metal oxides, sulfides, or nitrides typically have high impedance values and may be used in place of metals. Examples of these compounds are $SiO_2$, $LiGaO_2$, $Bi_{12}GeO_{20}$, $LiIO_3$, CdS, ZnO, AlN, $LiNbO_3$, $LiTaO_3$, $Ba_2NaNb_5O_{15}$, $BaTiO_3$, $PbTiO_3$, and $CaTiO_3$. Other examples of polymeric materials that may be used in the manufacture of the matching layer of the present invention are rubbers, epoxy, polyurethane, polyethylene, polypropylene, polybutylene, polyvinyl chloride, ploybiphenyl chloride, polymethylmethacrylate, polycarbonate, and the like. If, particulate polymeric materials are used, the particle size is preferably much less than the thickness of that particular polymeric sublayer. For example, the particle size is preferably about 5 times, more preferably about 10 times, and most preferably about 25 times smaller than the thickness of the sublayer. The sublayers also may be manufactured separately and then securely attached together to form the finished matching layer. Such an attachment may be accomplished by applying a very thin film or a thin performed mesh of adhesive material between the sublayers, applying a pressure on the entire assembly of sublayers, and curing the adhesive material. Suitable adhesive materials are thermoplastic polymers.

Figure 2:
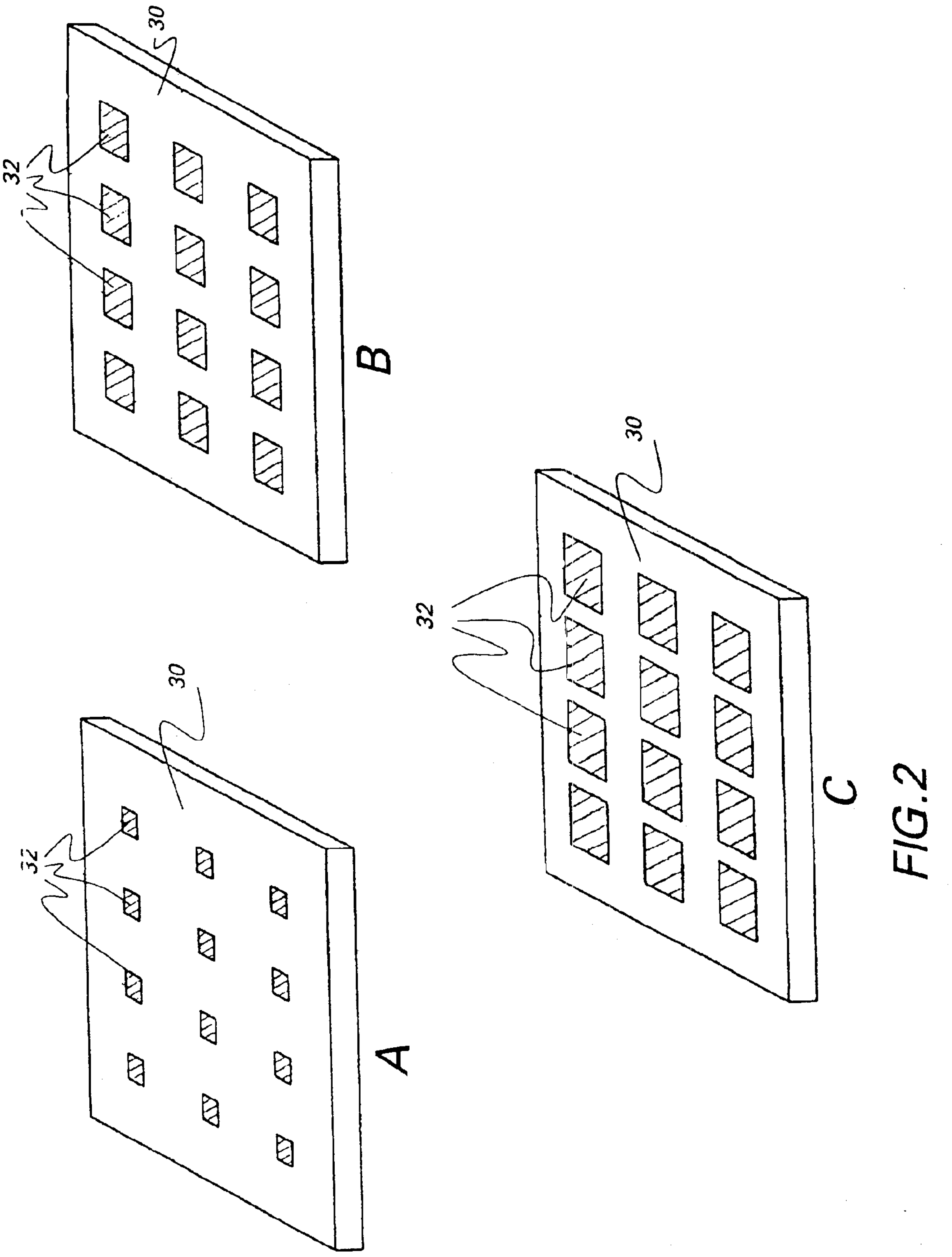
FIG. 2 shows embodiments of the sublayers in which a pattern is formed with different materials having different impedance values.

In a second embodiment, each sublayer may be formed in a pattern of different materials. For example, FIG. 2 shows a pattern of a sublayer. A first material, such as a metal, occupies the continuous area, and the second material, such as a polymer, occupies the discontinuous area, or vice versa. In addition, the total area occupied by each material may vary from one surface of the matching layer to the other surface so that the impedance values of the sublayers vary in the range from that of the transducer element material to that of the target. For example, in FIG. 2A, a material having an impedance close to that of the transducer element material occupies area 30, and a second material having an impedance close to that of the target occupies areas 32. This sublayer is positioned immediately adjacent to the transducer elements. The size of the areas 32 increases in the subsequent sublayers in the direction from the transducer elements to the target, as shown in FIGS. 2B and 2C. Patterns other than that shown in FIGS. 2A–2C may also be used. For example, the different materials may be formed in adjacent stripes having different widths. The sublayer may be formed by etching the pattern in a thin metal film and depositing a polymeric material in the etched-out areas. Such etching may be accomplished using the photolithography technique conventionally used in the production of microelectronic devices. Alternatively, the pattern may be formed by laser ablation of a polymeric thin film, and metal is deposited in the ablated areas. The individual sublayers are securely attached together, for example, by applying a thin adhesive layer between two adjacent sublayers, as was mentioned above.

In another embodiment of the present invention, the sublayers are formed successively, one on top of another, by a printing technique, such as inkjet printing or screen printing. For example, particles of a first material having a high impedance value may be dispersed in a liquid medium and printed in a desired pattern on a temporary substrate. The liquid medium may contain a temporary binder, such as starch, to promote the adherence of the particles. Particles of a second material having a low impedance value may be dispersed in the same or a different liquid medium and printed to fill the empty areas left during the printing of the first material to complete the first sublayer. Additional sublayers are formed successively on top of the first layer by the same printing technique. The pattern of each sublayer is chosen that impedance values of the sublayers vary monotonically.

In still another embodiment of the present invention, the sublayer may be formed by tape casting, slip casting, or gel casting. In this case, particles of materials having different impedance values, such as a metal or a ceramic powder and a polymer, are mixed together in a liquid medium in a composition that gives the desired final impedance value to the sublayer. The mixtures are applied successively, one on top of another, to form the final matching layer. The limitations of maximum packing density, desired impedance value, and manufacturability will govern the choice of the individual materials. Alternatively, the matching layer thus formed may be bisque-fired to sinter the metal or ceramic powder. Then, a polymeric material in a liquid medium may be infiltrated into the open pores to provide further mechanical integrity to the matching layer and to adjust the impedance value.

Figure 3:
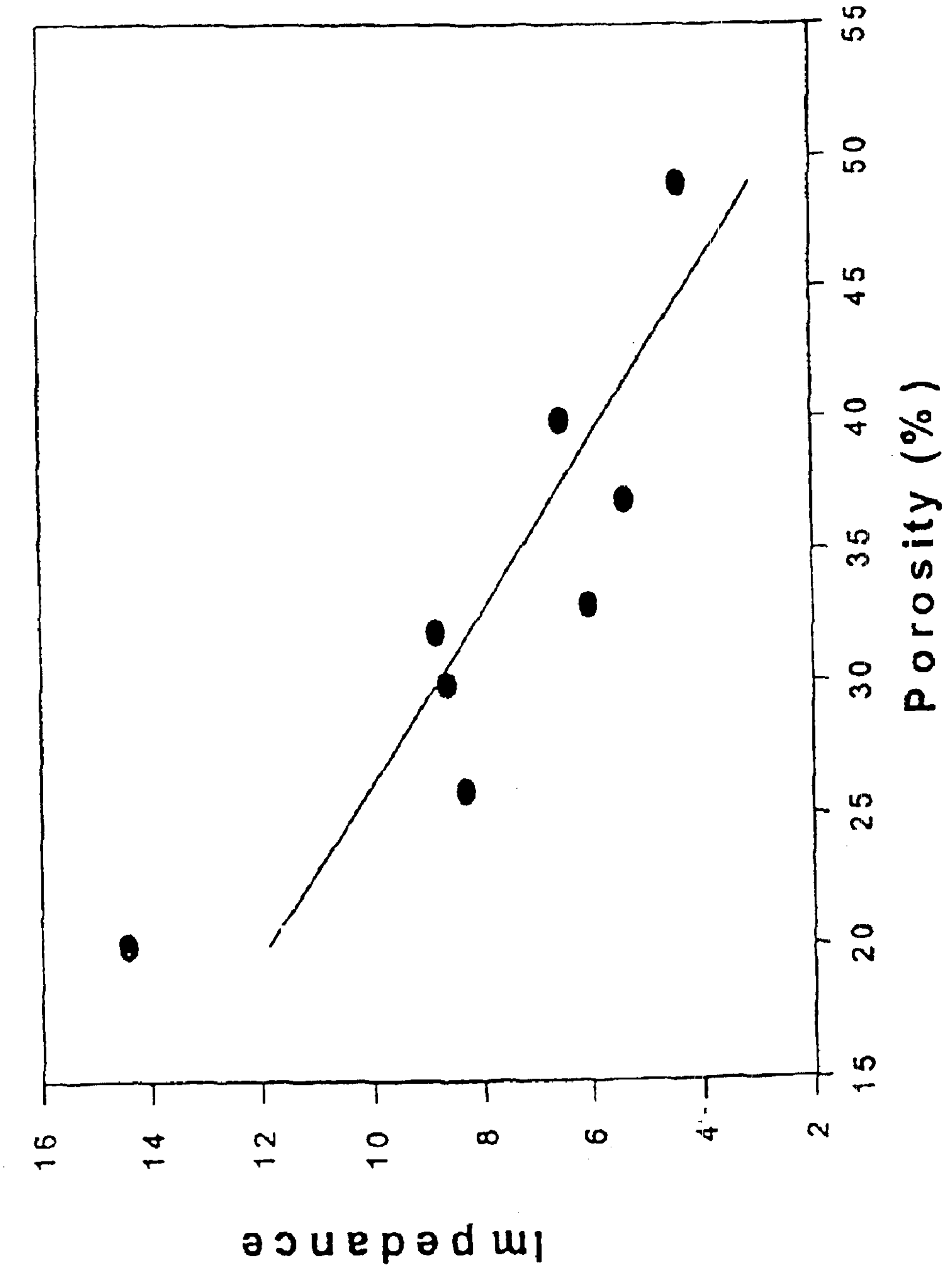
FIG. 3 shows the impedance values of samples of matching layers made of cement.

The inventors have discovered that various kinds of cement may be used either alone or in mixtures with other particulate materials to provide matching layers having controlled impedance values. These mixtures offer ease of forming sublayers. FIG. 3 shows impedance values of matching layers made of ordinary Portland cement with different initial water contents of the cement-water mixtures to yield different porosities. Table 1 shows that impedance values intermediate between that of the typical PZT transducer element material and that of the target were achieved. It can be inferred from Table 1 that sublayers having impedance values approaching that of the typical PZT transducer element material or that of the target may be made if other appropriate materials are selected to be mixed with the cements.

TABLE 1

| Components | Composition (wt %) | Water-to-Cement Ratio (by weight) | Density ($g/cm^3$) | Porosity (%) | Impedance (Mrayls) |
|---|---|---|---|---|---|
| OPC[1] | 10 | — | 9.0 | 29.3 | 26.2 |
| Tungsten | 90 | | | | |
| OPC | 20 | — | 6.8 | 27.9 | 22.9 |
| Tungsten | 80 | | | | |
| OPC | 50 | — | 4.0 | 24.8 | 15.2 |
| Tungsten | 50 | | | | |
| OPC | 70 | — | 3.0 | 28.0 | 13.6 |
| Tungsten | 30 | | | | |
| OPC | 90 | — | 2.5 | 27.6 | 10.7 |
| Tungsten | 10 | | | | |
| OPC | 12.5 | — | 4.5 | 30.9 | 9.7 |
| PZT | 87.5 | | | | |
| OPC | 11.1 | — | 4.5 | 31.5 | 8.5 |
| PZT | 88.9 | | | | |
| OPC | 19.0 | — | 3.6 | 33.4 | 8.2 |
| Fumed silica | 5.0 | | | | |
| PZT | 76.0 | | | | |
| OPC | 36.4 | 0.6 | 1.8 | 30.0 | 6.8 |
| Sand | 36.4 | | | | |
| Fumed silica | 3.8 | | | | |
| Water | 21.9 | | | | |
| SMF[2] | 1.5 | | | | |
| OPC | 34.3 | 0.8 | 1.7 | 50.0 | 5.0 |
| Alumina | 34.3 | | | | |
| Fumed silica | 3.6 | | | | |
| Water | 26.0 | | | | |
| SMF | 1.7 | | | | |
| OPC | 66.7 | 0.5 | 1.6 | 49.0 | 4.4 |
| Water | 33.3 | | | | |

Note:
[1]ordinary Portland cement
[2]sulfonated melamine formaldehyde

Since polymeric materials typically have low impedance values, they may be combined with cement to produce sublayers having impedance values less than about 4 Mrayls, thus approaching the impedance value of the typical target. Such a sublayer would provide a smooth transmission of energy from the ultrasound probe to the target.

Controlling the impedance of the sublayer by controlling its porosity is further illustrated in Table 2 in which the impedance is shown as a function of volume fraction occupied by the solid PZT material.

TABLE 2

| Volume Percent Occupied by PZT | Impedance (Mrayls) |
|---|---|
| 50 | 10.4 |
| 70 | 15.0 |
| 80 | 17.2 |
| 90 | 20.8 |

Thus, a sublayer having a controlled low impedance may be made by dispersing a very small amount of PZT particles in a polymeric material such as an epoxy, which has an impedance in the range of 1.3–3.0 Mrayls. Alternatively, a sublayer having a high pore volume fraction (i.e., a low volume percent occupied by PZT or other ceramic of metal oxides, metal sulfides, or metal nitrides mentioned above) is infiltrated with a material having a low impedance, such as a polymeric material, to produce a sublayer having a controlled low impedance. The highly porous ceramic sublayer may be formed by pressing ceramic particulates; with or without a temporary binder, such as a starch; into a thin sheet and sintering the sheet at a temperature exceeding about 900° C. The infiltration of the second material may be accomplished using a liquid form of the second material. Preferably, the liquid has a low surface tension, such as less than 150 dyne/cm, to facilitate the infiltration. Then the sublayers may be attached together using an adhesive as described above to produce the matching layer for the ultrasound probe.

While specific preferred embodiments of the present invention have been described in the foregoing, it will be appreciated by those skilled in the art that many modifications, substitutions, or variations may be thereto without departing from the spirit and scope of the invention as defined in the appended claims.

What is claimed is:

1. A matching layer for an ultrasound probe comprising a plurality of sublayers attached together, the sublayers having different impedance values, a first sublayer of the plurality of sublayers being disposed adjacent to an element of a transducer of the ultrasound probe, a last sublayer of the plurality of sublayers being disposed adjacent to a target, the impedance value of the first sublayer being less than or equal to the impedance value of the element of the transducer, the impedance value of the last sublayer being greater than or equal to the impedance value of the target, the impedance values of the sublayers decreasing from the first to the last sublayer, wherein each of said sublayers comprises a plurality of materials having different impedance values, and one of said materials is distributed in another of said materials.

2. The matching layer for an ultrasound probe of claim 1, wherein the impedance value of the first sublayer is within about 20 percent of the impedance value of the transducer element.

3. The matching layer for an ultrasound probe of claim 1, wherein the impedance value of the last sublayer is within 20 percent of the impedance value of the target.

4. The matching layer for an ultrasound probe of claim 1, wherein each of the sublayers has a thickness of less than about 100 $\mu$m.

5. The matching layer for an ultrasound probe of claim 1 wherein the matching layer has a thickness of about one-quarter wavelength of a central frequency of the transducer element when the transducer element is energized.

6. The matching layer for an ultrasound probe of claim 1 wherein the matching layer has a thickness equal to an odd multiple of one-quarter wavelength of a central frequency of the transducer element when the transducer element is energized.

7. The matching layer for an ultrasound probe of claim 6 wherein the odd multiple is smaller than or equal to 21.

8. The matching layer for an ultrasound probe of claim 1 wherein a sublayer is made of a composite material having at least two components, and each of said components comprises one material distributed in another material.

9. The matching layer for an ultrasound probe of claim 8 wherein the at least two components have different impedance values and each of the components forms a pattern in the sublayer.

10. The matching layer for an ultrasound probe of claim 9 wherein the sublayer is made by a process comprising the steps of:

forming a sheet of a first component, the sheet having a thickness of about one-quarter wavelength or an odd multiple of one-quarter wavelength of the central frequency of the transducer material;

forming openings in the sheet; and filling the openings with at least one other component.

11. The matching layer for an ultrasound probe of claim 10 wherein the first component comprises a material selected from the group consisting of nickel, aluminum, tin, lead, zinc, titanium, zirconium, iron, cobalt, copper, manganese, chromium, tungsten, gold, silver, magnesium, silicon, ceramics, metal oxides, metal sulfides, metal nitrides, glass, cement, mixtures thereof, and alloys thereof; and the at least one other component is selected from the group consisting of rubbers, epoxy, polystyrene, polyurethane, polyethylene, polypropylene, polybutylene, polyvinyl chloride, polybiphenyl chloride, polymethylmethacrylate, polycarbonate, copolymers thereof, and mixtures thereof.

12. The matching layer for an ultrasound probe of claim 10 wherein the first component comprises a material selected from the group consisting of rubbers, epoxy, polystyrene, polyurethane, polyethylene, polypropylene, polybutylene, polyvinyl chloride, polybiphenyl chloride, polymethylmethacrylate, polycarbonate, copolymers thereof, and mixtures thereof; and the at least one other component is selected from the group consisting of nickel, aluminum, tin, lead, zinc, titanium, zirconium, iron, cobalt, copper, manganese, chromium, tungsten, gold, silver, magnesium, silicon, ceramics, metal oxides, metal sulfides, metal nitrides, glass, cement, mixtures thereof, and alloys thereof.

13. The matching layer for an ultrasound probe of claim 8 wherein said one material and said another material are mixed together.

14. The matching layer for an ultrasound probe of claim 13 wherein a binder is mixed with said one material and said another material.

15. The matching layer for an ultrasound probe of claim 1, wherein the impedance value of the first sublayer is equal to the impedance value of the transducer element.

16. The matching layer for an ultrasound probe of claim 1, wherein the impedance value of the first sublayer is within 10 percent of the impedance value of the transducer element.

17. The matching layer for an ultrasound probe of claim 1, wherein the impedance value of the last sublayer is equal to the impedance value of the target.

18. The matching layer for an ultrasound probe of claim 1, wherein the impedance value of the last sublayer is within 10 percent of the impedance value of the target.

19. The matching layer for an ultrasound probe of claim 1 wherein each of the sublayers has a thickness of less than about 10 $\mu$m.

20. The matching layer for an ultrasound probe of claim 1 wherein each of the sublayers has a thickness of less than about 50 $\mu$m.

21. A method of making a matching layer for an ultrasound probe comprising the steps of:

forming a plurality of sublayers having different impedance values; and attaching the sublayers together such that a first sublayers, being disposed adjacent to an element of a transducer of the ultrasound probe, has an impedance value equal to or less than an impedance value of the transducer element; the last sublayer, being disposed adjacent to a target, has an impedance value greater than or equal to the impedance value of the target; and the impedance values of the sublayers decrease from the first to the last sublayer;

wherein the forming of each of the sublayers comprising the steps of:

forming a sheet comprising a first material distributed in a second material;

forming openings in the sheet; and filling the openings with a third material having a different impedance than the impedance of the first material.

22. The method of making a matching layer for an ultrasound probe of claim 21 wherein the step of forming the sheet comprising the first material and the second material is done by a method selected from the group consisting of electroplating, electrophoresis, tape casting, slip casting, and gel casting; the step of forming openings in the sheet is done by leaving empty areas in the sheet; and the step of filling the openings is done by a method selected from the group consisting of spraying, inkjet printing, screen printing, tape casting, slip casting, and gel casting.

23. The method of making a matching layer for an ultrasound probe of claim 21 wherein the first material is selected from the group consisting of nickel, aluminum, tin, lead, zinc, titanium, zirconium, iron, cobalt, copper, manganese, chromium, tungsten, gold, silver, magnesium, silicon, ceramics, metal oxides, metal sulfides, metal nitrides, glass, cement, mixtures thereof, and alloys thereof; and the third material is selected from the group consisting of rubbers, epoxy, polyurethane, polyethylene, polypropylene, polybutylene, polyvinyl chloride, polybiphenyl chloride, polymethylmethacrylate, polycarbonate, copolymers thereof, and mixtures thereof.

24. A method of making a making a matching layer for an ultrasound probe comprising the steps of:

forming a first sublayer on a temporary substrate;

forming at least one other sublayer on the first sublayer to provide a plurality of sublayers comprising a first and a last sublayer, the plurality of sublayers being attached together; and removing the plurality of sublayers from the substrate;

wherein each sublayer comprises particles of one material dispersed in another material, and impedance values of the sublayers change monotonically from the first to the last sublayer.

25. The method of making a matching layer for an ultrasound probe of claim 24 wherein the step of forming the sublayers is done by a method selected from the group consisting of inkjet printing, screen printing, tape casting, slip casting, gel casting, electrophoresis, and electroplating.

26. The method of making a matching layer for an ultrasound probe of claim 25 wherein each sublayer is a composite of at least two materials having different impedance values and the composite has a composition selected such that impedance values of the sublayers as arranged in the matching layer change monotonically from the first to the last sublayer.

27. A method of making a matching layer for an ultrasound probe comprising the steps of:

providing a first material in a particulate form, the first material having a first impedance value;

forming a plurality of sheets of the particulate first material; said plurality of sheets having different porosities;

sintering the particulate first material to produce porous sheets of the first material;

infiltrating the porous sheets of the first material with a liquid of a second material having a second impedance value different from the first impedance value;

solidifying the second material to form a plurality of sublayers having varying sublayer impedance value;

attaching the sublayers together to form the matching layer for an ultrasound probe in an order such that the sublayers impedance value varies monotonically through the matching layer.

28. The method of making a matching layer for an ultrasound probe of claim 27 wherein the first material has a higher impedance value that the second material.

29. The method of making a matching layer for an ultrasound probe of claim 27 wherein the first material is selected from the group consisting of nickel, aluminum, tin, lead, zinc, titanium, zirconium, iron, cobalt, copper, manganese, chromium, tungsten, gold, silver, magnesium, silicon, ceramics, metal oxides, glass, cement, mixtures thereof, and alloys thereof; and the second material is selected from the group consisting of rubbers, epoxy, polyurethane, polyethylene, polypropylene, polybutylene, polyvinyl chloride, polybiphenyl chloride, polymethylmethacrylate, polycarbonate, copolymers thereof, and mixtures thereof.

* * * * *